United States Patent
Ogi et al.

(10) Patent No.: US 12,216,954 B2
(45) Date of Patent: Feb. 4, 2025

(54) IMAGE DISPLAY METHOD AND RECORDING MEDIUM

(71) Applicant: SCREEN HOLDINGS CO., LTD., Kyoto (JP)

(72) Inventors: Hiroshi Ogi, Kyoto (JP); Saya Shibata, Kyoto (JP); Tomoyasu Furuta, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 154 days.

(21) Appl. No.: 18/088,992

(22) Filed: Dec. 27, 2022

(65) Prior Publication Data

US 2023/0205475 A1 Jun. 29, 2023

(30) Foreign Application Priority Data

Dec. 28, 2021 (JP) .................. 2021-214955

(51) Int. Cl.
*G06F 3/14* (2006.01)
*G06F 3/0482* (2013.01)
(Continued)

(52) U.S. Cl.
CPC .............. *G06F 3/14* (2013.01); *G06F 3/0482* (2013.01); *G06F 3/04842* (2013.01);
(Continued)

(58) Field of Classification Search
CPC ...... G06F 3/14; G06F 3/04842; G06F 3/0482; G16H 30/40; G16H 40/63; G06T 2207/30024; G06T 7/0012; G06T 7/30
See application file for complete search history.

(56) References Cited

U.S. PATENT DOCUMENTS

2010/0111396 A1* 5/2010 Boucheron ............. G06F 18/29
  382/133
2012/0093385 A1 4/2012 Yokosawa et al.
(Continued)

FOREIGN PATENT DOCUMENTS

CN 102802519 B 12/2014
CN 108140249 A 6/2018
(Continued)

OTHER PUBLICATIONS

Extended European Search Report, Application No. 22215891.7, Apr. 28, 2023, 10 pages.
(Continued)

*Primary Examiner* — Muhammad N Edun
(74) *Attorney, Agent, or Firm* — Rimon P.C.

(57) ABSTRACT

An image display method according to this invention includes obtaining an image set including a plurality of stained images, the plurality of stained images being obtained by imaging a multiple immunostained tissue specimen, a registration processing being performed for mutual registration for the plurality of stained images, and switching and displaying the stained images included in the image set on a screen in accordance with a predetermined switch rule with a result of the registration processing reflected. An image includes at least one of the stained images and a graphical user interface for receiving an operation input from a user for editing the switch rule being displayed on the screen. The switch rule is changed and set according to the operation input. The image is displayed on the screen in accordance with the changed and set switch rule.

11 Claims, 10 Drawing Sheets

(51) Int. Cl.
  *G06F 3/04842* (2022.01)
  *G06T 7/00* (2017.01)
  *G06T 7/30* (2017.01)

(52) U.S. Cl.
  CPC .............. *G06T 7/0012* (2013.01); *G06T 7/30* (2017.01); *G06T 2207/30024* (2013.01)

(56) References Cited

U.S. PATENT DOCUMENTS

| | | | |
|---|---|---|---|
| 2015/0055844 A1* | 2/2015 | Molin | G06T 3/4053 382/131 |
| 2016/0371834 A1 | 12/2016 | Watanabe et al. | |
| 2017/0372118 A1 | 12/2017 | Schoenmeyer et al. | |
| 2018/0322632 A1 | 11/2018 | Barnes et al. | |
| 2019/0336033 A1 | 11/2019 | Takeshima | |
| 2021/0104070 A1* | 4/2021 | Mitsui | G06V 10/82 |
| 2022/0170940 A1 | 6/2022 | Ong et al. | |

FOREIGN PATENT DOCUMENTS

| | | |
|---|---|---|
| CN | 110121293 A | 8/2019 |
| TW | I689944 B | 4/2020 |
| TW | 202102207 A | 1/2021 |
| WO | 2015/002082 A1 | 1/2015 |
| WO | 2017036921 A1 | 3/2017 |
| WO | 2019108695 A1 | 6/2019 |

OTHER PUBLICATIONS

Taiwanese Office Action issued in corresponding Taiwanese Patent Application No. 111139960, dated Aug. 9, 2023.

* cited by examiner

IMAGE DISPLAY METHOD AND RECORDING MEDIUM

CROSS REFERENCE TO RELATED APPLICATION

The disclosure of Japanese Patent Application No. 2021-214955 filed on Dec. 28, 2021 including specification, drawings and claims is incorporated herein by reference in its entirety.

BACKGROUND OF THE INVENTION

1. Field of the Invention

This invention relates to a display method for a stained image obtained by imaging a multiple immunostained tissue specimen and particularly to a method for displaying a stained image including a result of a registration processing for registration between stained images.

2. Description of the Related Art

In the field of immunohistochemistry of recent years, attention has been paid to a so-called single cell analysis, which not only sees a specimen as a group of cells, but also measures expression levels, positions and the like of biological materials such as proteins and their related materials for each cell, focusing on the individual cells constituting the group. For this purpose, image cytometry for imaging a tissue specimen and analyzing the tissue specimen by an image processing has been put to a practical use. In an analysis technique for a multiple immunostaining method using image cytometry, a plurality of specimen images corresponding to a plurality of types of staining are obtained by repeating staining, imaging and decoloring for a biological specimen such as a tissue section collected from a living body or an artificially cultured cell tissue.

In this technique, the specimen images need to be registered (registration processing) to enable cross-reference of the plurality of specimen images to which mutually different types of staining were applied. A function of finding out mutually corresponding parts of images and obtaining a position shift amount between those found-out parts in a set (image stack) composed of a plurality of images has been more often implemented in general image processing software. Further, a technique described, for example, in WO2015/002082 (patent literature 1) is known as a registration technique specialized for tissue specimen images.

In multiple immunostaining in which various staining methods are successively applied, modes of expression of staining results largely differ among stained images. There are possibly such combinations in which no corresponding parts are found between the images. Thus, with the conventional registration processing technology, all the stained images cannot be always correctly registered, i.e. there are cases where registration fails.

However, a technique for automatically determining a success or failure of registration between stained images having different image contents as just described has not been established yet and an operation of a skilled person to judge a success or failure by the eyes is still necessary. Further, such judgment is not easy also for the skilled person and a workload becomes enormous if the number of types of staining increases. From this, it is desired to establish a technique capable of supporting a confirmation operation by a user for a result of a registration processing and efficiently performing this operation. Such a technique has also not been proposed thus far yet.

SUMMARY OF THE INVENTION

This invention was developed in view of the above problem and aims to provide an image display method capable of effectively supporting a user operation of confirming a result of a registration processing between a plurality of stained images obtained by imaging a multiple immunostained tissue specimen.

One aspect of an image display method according to this invention includes obtaining an image set including a plurality of stained images, the plurality of stained images being obtained by imaging a multiple immunostained tissue specimen, a registration processing being performed for mutual registration for the plurality of stained images, and switching and displaying the stained images included in the image set on a screen in accordance with a predetermined switch rule with a result of the registration processing reflected, an image including at least one of the stained images and a graphical user interface for receiving an operation input from a user for editing the switch rule being displayed on the screen, the switch rule being changed and set according to the operation input, and the image being displayed on the screen in accordance with the changed and set switch rule.

Here, the "switch rule" is a rule for determining which image, out of the respective stained images, should be displayed in which order in the screen display. In the invention, this switch rule is dynamically changeable by a user operation. Further, the registration processing is a processing performed to correct a relative position shift between the respective images. It may be a processing until a position shift amount is obtained or may be a processing including a position correction corresponding to the obtained position shift amount.

A method for switching and displaying a plurality of images having similar contents and making the presence or absence and degrees of change of differences between the images easily visually confirmable using an afterimage effect is widely adopted. However, a method using this principle for the purpose of confirming results of the registration processing of the multiple immunostained images has not been put to a practical use yet. A main reason for that is thought as follows. The confirmation of differences using the afterimage effect is effective when differences between images are relatively small. However, the afterimage effect does not necessarily effectively function in an image set in which content differences are large between images such as multiple immunostained images.

For a plurality of stained images included in an image set, if the images having similar image contents are combined and successively switched and displayed, the confirmation of differences is thought to become easier. More specifically, the images expressly including parts corresponding to each other can be used. However, a method itself for comparing a plurality of stained images with each other and combining the stained images in a proper display order according to degrees of similarity does not exist.

Accordingly, in the invention configured as described above, the switch rule such as a combination of the stained images to be switched and displayed and the arrangement of the stained images is determined based on the operation input from the user, and the focus is to provide the user interface for efficiently performing an operation at that time.

Specifically, the image set to be switched and displayed includes the plurality of stained images obtained by imaging the multiple immunostained tissue specimen, and the registration processing is performed in advance between those stained images. When the stained images are switched and displayed on the screen, the result of the registration processing is reflected on each stained image. That is, when a switch is made from the currently displayed stained image to the next stained image, the next stained image is displayed with a relative position shift from the preceding stained image eliminated. By reflecting the result of the registration processing on the switch display in this way, the user can confirm a success or failure of the registration processing by comparing the images before and after the switch.

A combination of the images before and after the switch is changeable by the user operating the graphical user interface (GUI) displayed together with the stained image. A technique for this can be, for example, made similar to a widely used method for rearranging image files listed and displayed in a window.

As just described, in this invention, the plurality of stained images included in the image set are switched and displayed while the result of the registration processing is reflected. At this time, the GUI for editing the switch rule is displayed together with these. If the switch rule is changed by the user operation, the switch display is performed in accordance with the changed switch rule. Therefore, the user can compare the images, specifically confirm a success or failure of the registration processing, by combining, switching and displaying the images desired to be compared, out of the plurality of stained images.

As described above, in the invention, for an image set including a plurality of stained images obtained by multiple immunostaining and imaging associated with that, the respective stained images are switched and displayed while the results of the registration processings are reflected on the stained images. A combination of the images before and after the switch is changeable by an operation input from a user via the GUI. By these functions, it is possible to effectively support a user operation of confirming the result of the registration processing between the plurality of stained images and reduce a user workload.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

DETAILED DESCRIPTION OF THE PREFERRED EMBODIMENTS

An image display processing, which is one embodiment of an image display method according to the invention, is described below. This image display processing is executable by a system provided with a processor having an image processing function and a logical operation function, an input device for receiving an operation input from a user and an image display device, and can be executed, for example, using a personal computer device having a general hardware configuration. A mouse, a keyboard, a stylus pen and the like can be used singly or in appropriate combination as the input device. Further, a liquid crystal display device can be, for example, used as the image display device. A touch screen including both an input device and an image display device may be used.

An object of this image display processing is an image set including a plurality of stained images obtained by imaging a multiple immunostained tissue specimen and further performing a registration processing. This embodiment functions particularly effectively for the image set including three or more stained images. The image set is generated as follows.

Figure 1:
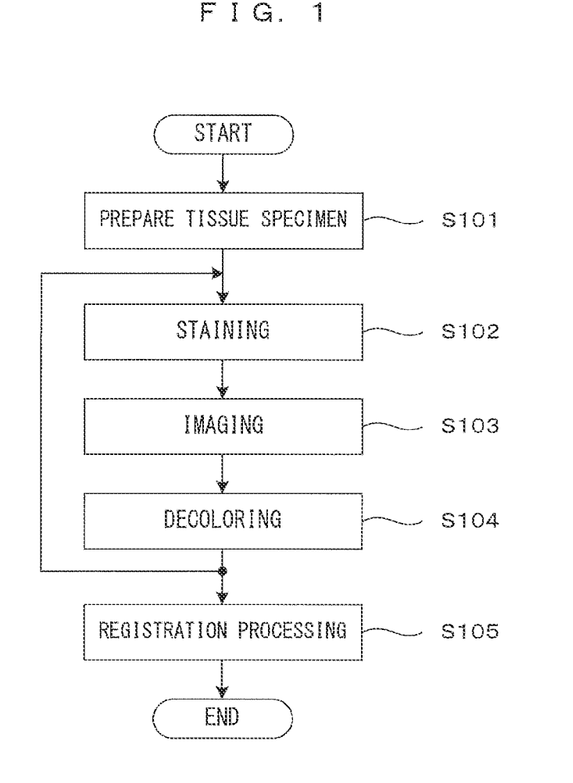
FIG. 1 is a flow chart outlining a process of generating the image set.

FIG. 1 is a flow chart outlining a process of generating the image set. First, a tissue specimen to be analyzed is prepared (Step S101). The tissue specimen is a specimen, such as a tissue removed from a living body or cultured cells, fixed to an appropriate carrier such as a cover glass. Staining (Step S102), imaging (Step S103) and decoloring (Step S104) are performed for each of a plurality of types of staining methods for the tissue specimen. In this way, the plurality of stained images are obtained by staining one tissue specimen by the plurality of types of staining methods and imaging the stained tissue specimen.

A position shift may occur between these stained images due to the repeated decoloring and staining operations between imaging operations, deformation of the specimen itself over time and the like. To correct this position shift, the registration processing is performed (Step S105). A relative movement amount necessary to properly overlap another image on one image is obtained as a "registration amount" in the registration processing. Various image processing algorithms for the registration processing have been put to a practical use and the type of the algorithm does not matter here. One set of images finished with the registration processing in this way is the "image set" mentioned here.

In multiple immunostaining, a light-and-shade pattern may be largely different from other stained images depending on images since cells to be stained are different. Due to this, it may be difficult to automatically and accurately register all the stained images. Thus, it remains necessary for a user having a specialized knowledge to visually confirm the result of the registration processing. The image display method of this embodiment described below supports an operation in image display so that such a confirmation operation of the registration processing result by the user can be efficiently performed. A final purpose is to generate an image set succeeded in registration among all the images.

Figure 2:
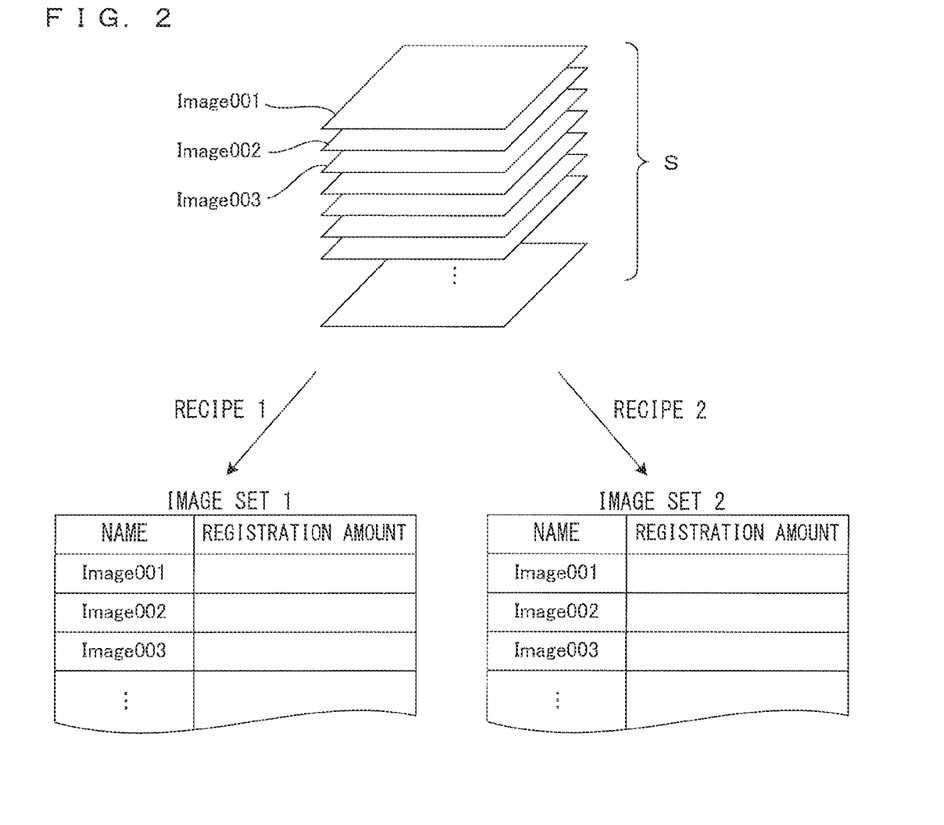
FIG. 2 is a view showing an example of the image set handled.

FIG. 2 is a view showing an example of the image set handled by this embodiment. By imaging the same region of the same tissue specimen in different stained states, an image stack S is obtained which includes a plurality of stained images Image001, Image002, Image 003, etc. An image set is configured by giving information on a registration amount obtained as a result of a registration processing to each of these stained images. The registration amount can be, for example, expressed by a relative parallel movement amount, rotation amount and the like between images necessary to correctly overlap two images.

A plurality of registration processings having mutually different processing conditions such as different processing algorithms or different parameter settings with the same algorithm are applicable to one image stack S. That is, one image stack S can generate a plurality of image sets. In the following example, it is assumed that two image sets (image set 1, image set 2) are generated in correspondence with two types of processing recipes (recipe 1, recipe 2) specifying processing contents of the registration processing.

Figure 3:
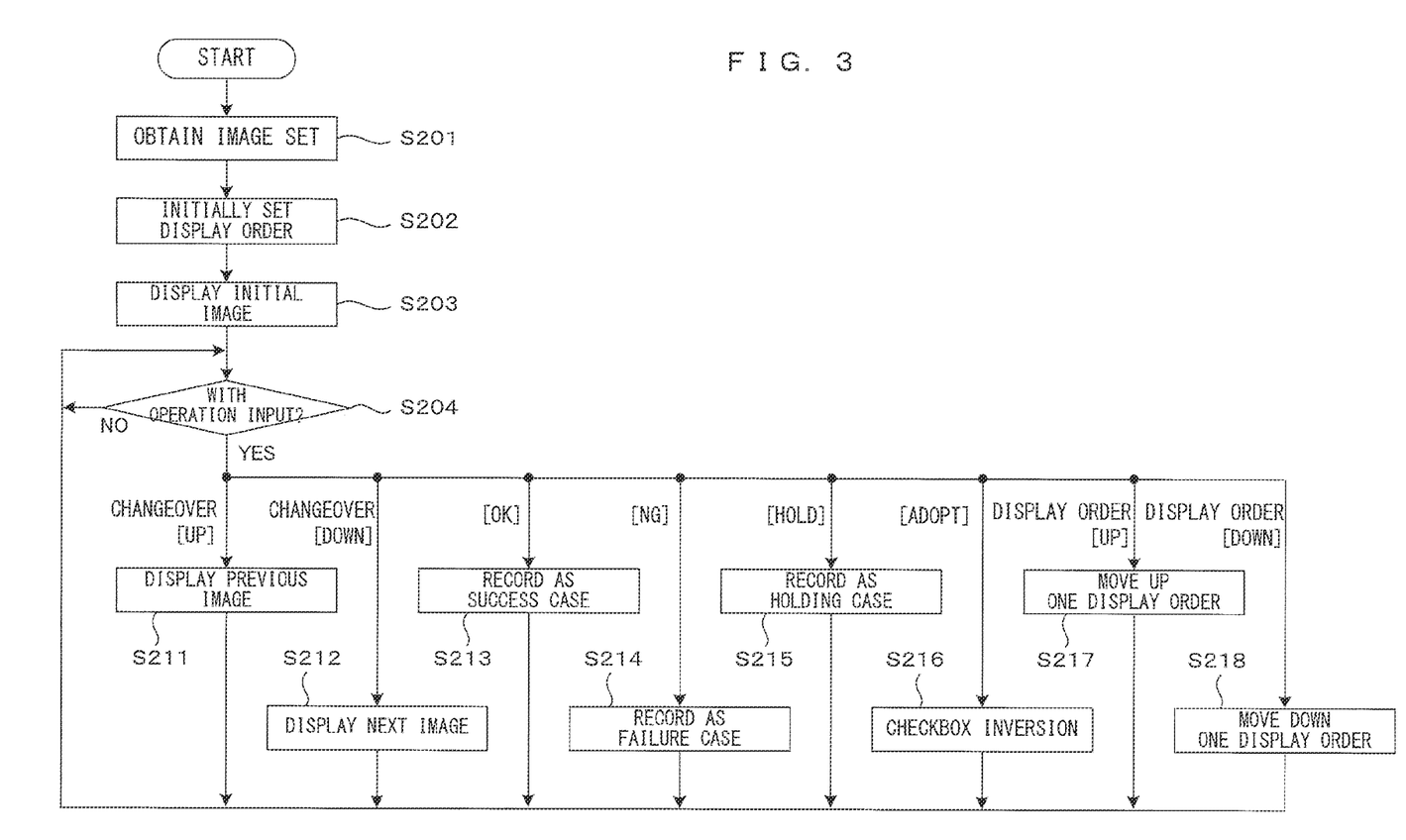
FIG. 3 is a flow chart showing the image display processing.

FIG. 3 is a flow chart showing the image display processing in this embodiment. This processing is realized, for example, by a computer device executing a control program prepared in advance. More specifically, the computer device displays a predetermined image on an image display device in accordance with the control program, receives an operation input from a user to an input device as needed and changes a display according to the received operation input.

First, the image set generated as described above is obtained (Step S201), and a display order of the plurality of stained images is initially set (Step S202). The display order at this time is arbitrary. The display order may be, for example, the same as an imaging order or a result of appropriate sorting based on results of a registration processing. An initial image including the stained image set in the first place in the display order is displayed on a screen of the image display device (Step S203). It is waited in this state until an operation input is given from the user (Step S204).

Figure 4:
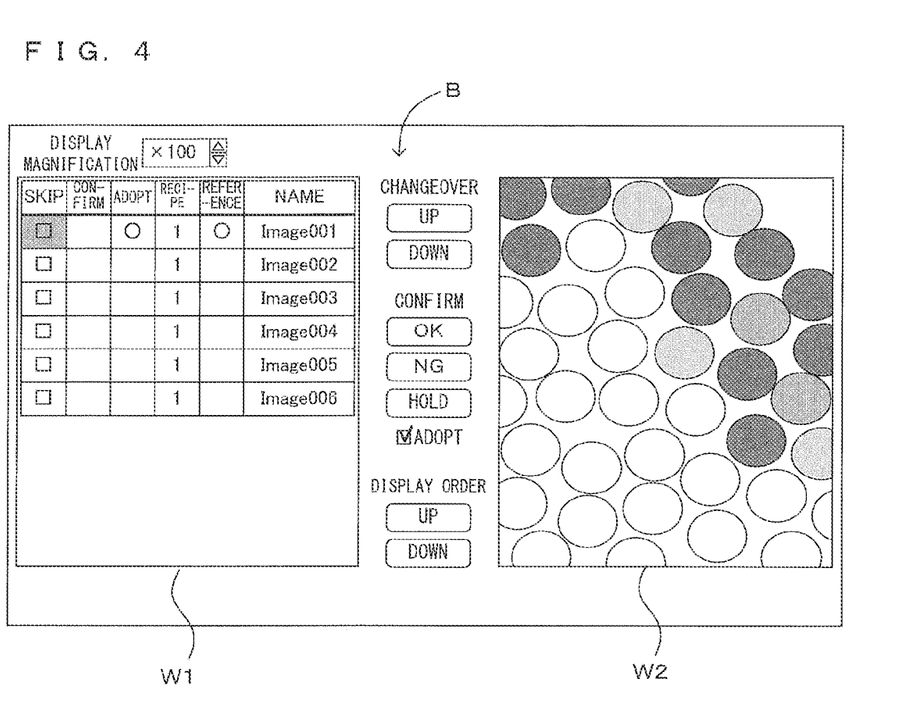
FIG. 4 is a view showing a configuration example of a display image.

FIG. 4 is a view showing a configuration example of a display image. The displayed image includes a list window W1 showing a list of images constituting the image set, an image window W2 displaying one designated image and a group of buttons B serving as a graphical user interface (GUI) for receiving an operation input from the user via the input device.

A list of file names of the stained images included in the obtained image set is displayed according to the currently set display order in the list window W1. Columns "SKIP", "CONFIRM", "ADOPT", "RECIPE" and "REFERENCE" are columns for reflecting the user operation. Information for specifying the recipe of the registration processing applied to the image set is displayed in the column "RECIPE", out of these columns. In this example, the application of the recipe 1 is indicated. The details of the other columns are described later. The selected stained image is displayed at an appropriate magnification in the image window W2. The column "SKIP" of the image Image001 painted out in dark color in the list window W1 indicates that the image currently displayed in the image window W2 is this image Image001. The display magnification is changeable by a user operation.

The group of buttons B includes changeover (display change over) buttons ("UP", "DOWN"), confirm buttons ("OK", "NG" and "HOLD") for receiving user's judgment on the result of the registration processing, an "ADOPT" check box for reflecting this image on an adopt window to be described later, and buttons ("UP", "DOWN") for changing the display order.

Referring back to FIG. 3, when an operation input to any of these buttons is given from the user (YES in Step S204), an operation thereafter differs depending on an operation content. Specifically, when the changeover button "UP" is handled, Step 5211 is performed.

On the other hand, when the changeover button "DOWN" is handled, Step 5212 is performed.

Similarly, when the confirm button "OK", "NG" or "HOLD" is handled, Step 5213, S214 or S215 is respectively performed. Further, if the "ADOPT" check box is clicked, Step S216 is respectively performed. Further, when the display order button "UP" or "DOWN" is handled, Step S217 or S218 is performed.

Figure 5:
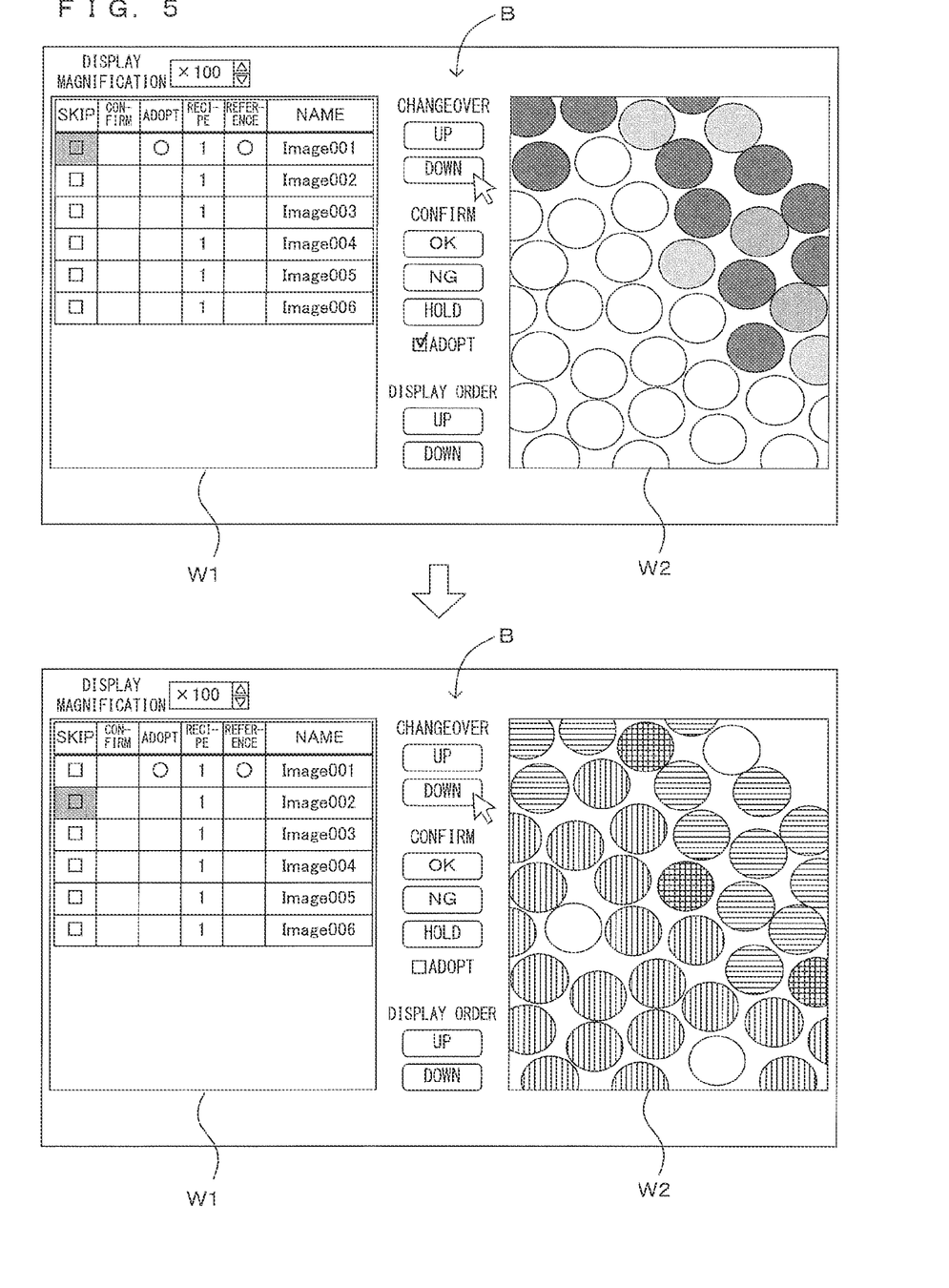
FIG. 5 is a view showing an operation example when the changeover button is handled.

FIG. 5 is a view showing an operation example when the changeover button is handled. It is assumed that the changeover button "DOWN" is handled, for example, by a mouse operation of the user with the image image001 displayed in the image window W2 as shown in an upper part of FIG. 5. This button is a button for displaying the image one below the image currently displayed in the image window W2 in the set display order. Accordingly, if this button is handled, an image in the image window W2 is switched to the image Image002 one below from the current image Image001 in the display order as shown in a lower part of FIG. 5 (Step S212). Associated with this, the dark color in the SKIP column is changed from the image Image001 to the image Image002 in the list window W1.

At this time, the result of the registration processing is reflected on the displayed image. That is, when the image in the image window W2 is switched from the image Image001 to the image Image002, a position correction for cancelling a relative position shift amount from the image Image001 obtained by the registration processing is applied to the image Image002.

If the button "DOWN" is handled again from this state, the image in the image window W2 is switched to the image Image003 (Step S212). On the other hand, if the button "UP" is handled, the image displayed in the image window W2 is switched from the image Image002 to the image Image001 (Step S211). In this way, the changeover buttons are for realizing a function of switching the stained image displayed in the image window W2 in accordance with the order displayed in the list window W1.

If the button "DOWN" is handled with the last stained image in the currently set display order displayed, the display may be switched to the leading stained image in the display order. Conversely, if the button "UP" is handled with the leading stained image displayed, the display may be switched to the last stained image. By so doing, the stained images distant from each other in the display order can be switched and compared.

When two stained images in different stained states are compared, it may be more effective to alternately display the two images by switching those with time than to display those side by side. This is because it becomes possible to evaluate the presence or absence or a degree of a position shift between the two images using an afterimage effect. By switching the images reflecting the result of the registration processing, a success/failure determination operation of the result of the registration processing by the user can be supported. That is, the user can confirm a success or failure of the result of the registration processing based on whether or not a position shift between the images before and after the switch is sensed.

Figure 6:
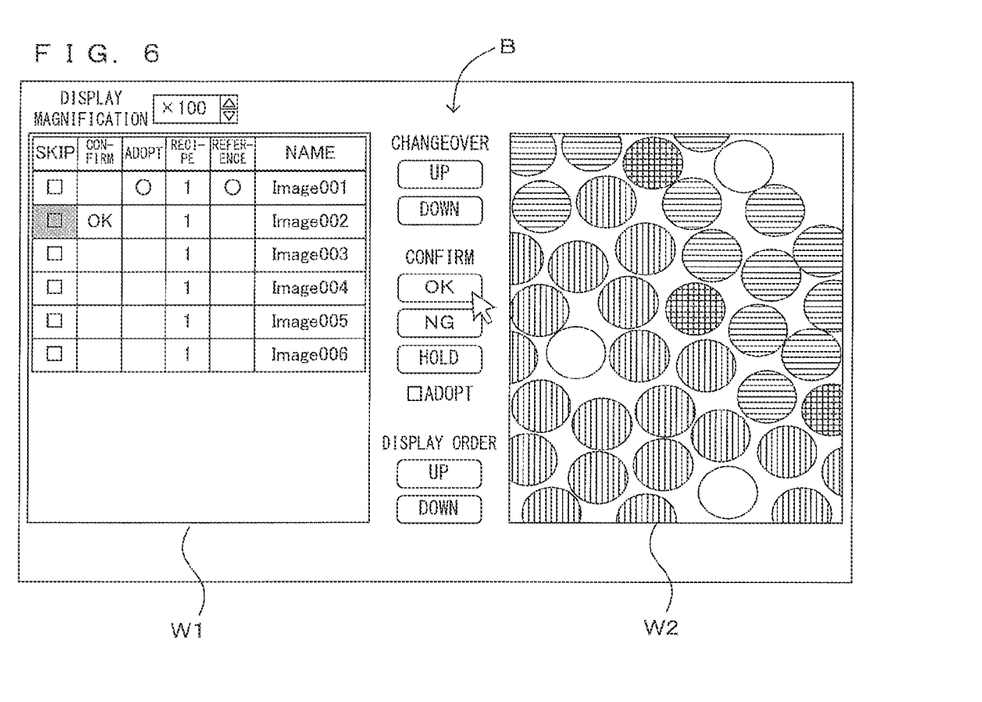
FIG. 6 is a view illustrating the success/failure determination operation of the registration processing by the user.

FIG. 6 is a view illustrating the success/failure determination operation of the registration processing by the user. The user can determine the success or failure of the registration processing by viewing the images switched and displayed. A determination result can be reflected on data. That is, if the success of the registration processing is determined, "OK" is shown in the column "CONFIRM" of the image displayed in the list window W1 if the user handles the confirm button "OK" as shown in FIG. 6. In this way, this image is recorded as an example in which the registration processing has succeeded (Step S213).

On the other hand, when an evident position shift is sensed and the user determines the failure of the registration processing, the registration processing of this image is recorded as a failed example (Step S214) by being handled the "NG" button. At this time, "NG" is shown in the column "CONFIRM" of this image displayed in the list window W1. An image, for which a success or failure is unclear, can be recorded as an example of "HOLD" (Step S215). In this way, it is, for example, possible to extract only the held images and separately perform a confirmation operation.

Figure 7:
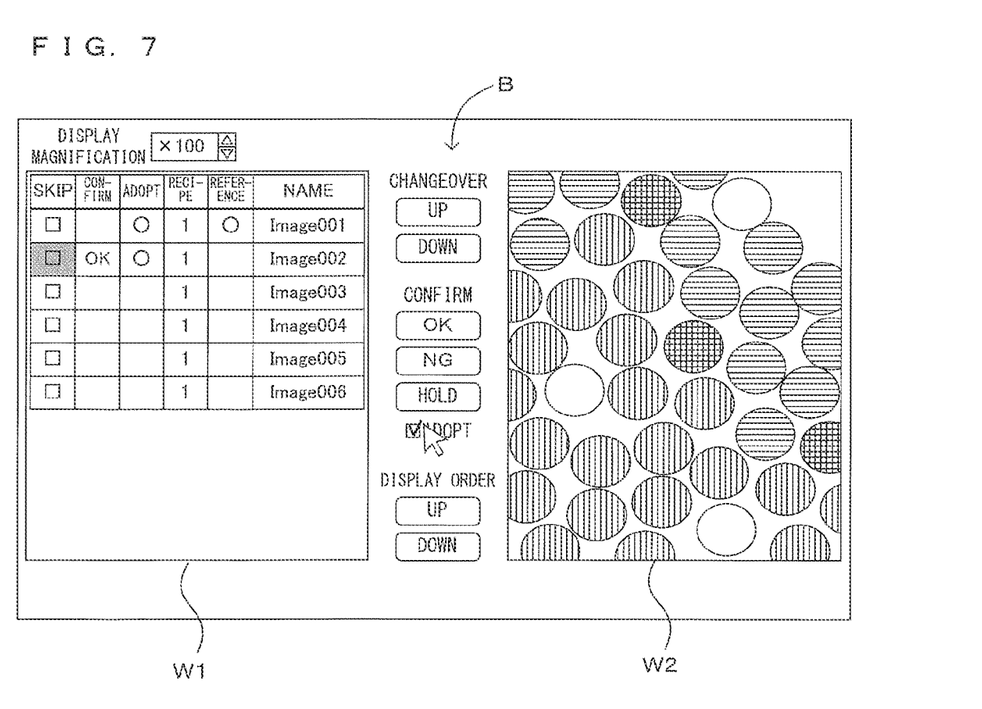
FIG. 7 is a view illustrating an operation to the check box "ADOPT" by the user.

FIG. 7 is a view illustrating an operation to the check box "ADOPT" by the user. If the user clicks the check box "ADOPT", a state where the check box is checked (hereinafter, referred to as an "adopted state") and a state where the check box is not checked (hereinafter, referred to as a "non-adopted state") can be switched from each other (Step S216). A function of the check box "ADOPT" is described later. A result of the operation to the check box is reflected in the column "ADOPT" in the list window W1. That is, a mark "○" is displayed in the column "ADOPT" for the image in the adopted state.

Figure 8:
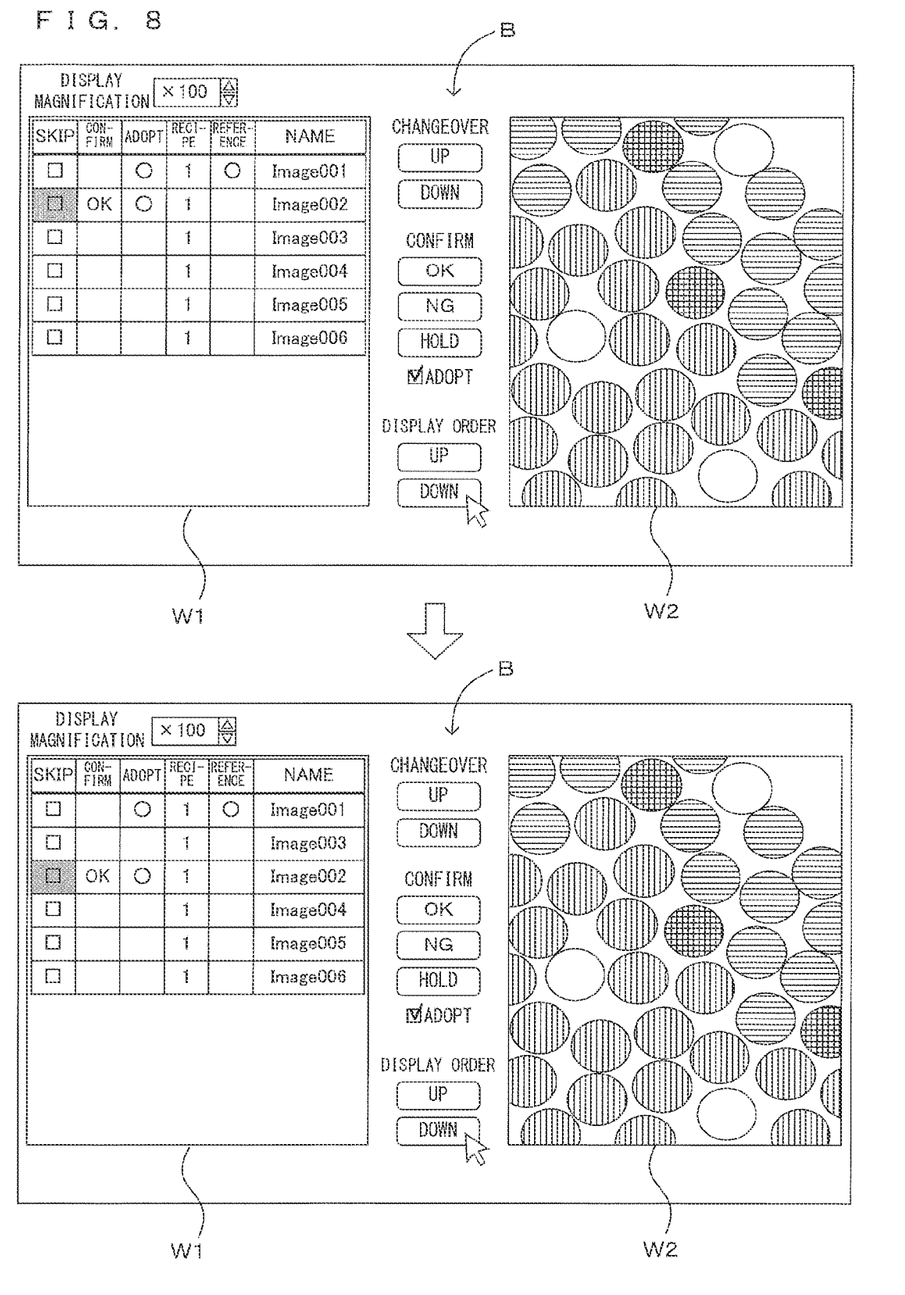
FIG. 8 is a view illustrating a display order operation by the user.

FIG. 8 is a view illustrating a display order operation by the user. For example, if the user handles the display order button "DOWN" with the image Image002 displayed in the image window W2 as shown in an upper part of FIG. 8, the display order of the image Image002 in the list window W1 is retarded by one as shown in a lower part of FIG. 8 (Step S218). As a result, the orders of the images Image002 and Image003 are switched. When the display order button "UP" is handled, the display order of this image is advanced by one (Step S217). As just described, the display order of the stained images can be changed by the user operation.

When two images are compared by switching and displaying the images, if the images before and after the switch include a common feature, the presence or absence of a position shift is easily determined using this feature as a clue. However, light-and-shade patterns of images may largely differ depending on stained contents in multiple immunostained images and no relevance between the images before and after the switch is found in many cases. From this, the display order of the stained images is made changeable by the user operation in this embodiment. By so doing, a combination of the images to be displayed before and after the switch can be selected by the user. As a result, an environment in which the success/failure determination is easily made such as the collection of related images or the arrangement of the images in the increasing order of the position shifts, for example, can be prepared by the user's judgment.

Further, there is also, for example, a need for setting one stained image in the image stack S as a reference image and performing a confirmation operation by successively comparing other two or more stained images with the reference image. Also in this case, the confirmation operation by switching and displaying the other images can be efficiently performed by successively moving the position of the reference image in the display order. A mark "○" is displayed in the column "REFERENCE" of the list window W1 for the stained image used as the reference image in the registration processing. In this example, it is indicated that the image Image001 was used as the reference image.

When the confirmation operation is performed while many images are switched, if there is an image having a low relevance among a plurality of mutually related images, it is difficult to judge the relevance in the images before and after this image. Such an image can be made not to immediately appear in a series of the switched and displayed images by changing the display order as described above. Besides this, also a method for excluding some images from images to be switched and displayed as described next is applicable.

Figure 9:
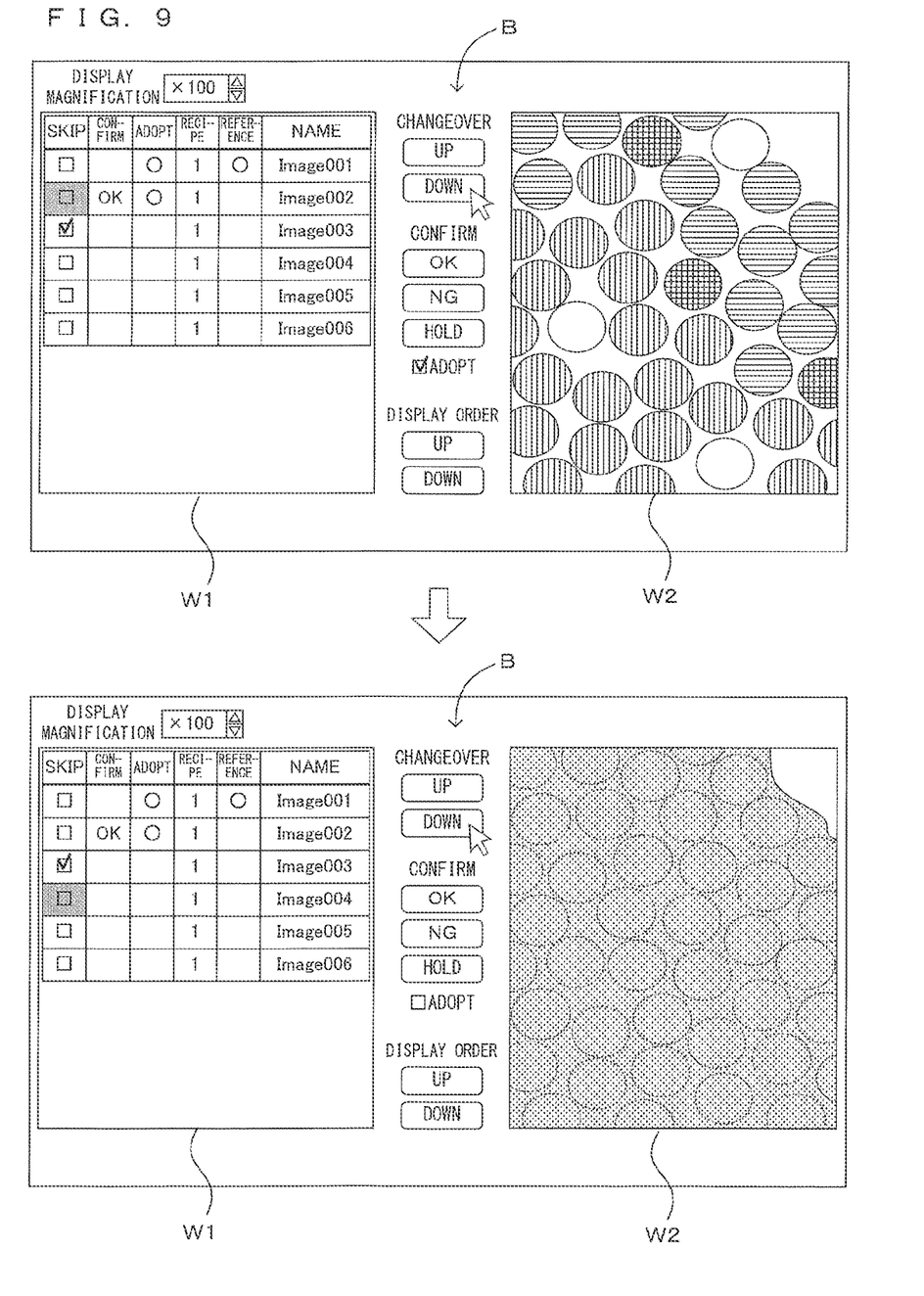
FIG. 9 is a view showing a skip processing of the image in switching the display.

FIG. 9 is a view showing a skip processing of the image in switching the display. As shown in an upper part of FIG. 9, the user can exclude a specific image from the images to be displayed by checking the column "SKIP" of the list window W1. When the user handles the changeover button "DOWN", for example, with the column "SKIP" of the image Image003 checked as shown in FIG. 9, the image to be displayed in the image window W2 is switched from the image Image002 to the image Image004 and the display of the image Image003 is skipped. Further, if the changeover button "UP" is handled from this state, a switch is made from the image Image004 to the image Image002.

For example, the image judged to have been failed in the registration processing may become rather an obstacle of the confirmation operation of the other images by appearing in the switch display. By excluding such an image from the images to be switched and displayed, the confirmation operation using the afterimage effect can smoothly proceed. The image excluded from the images to be displayed in this way can be returned to the image to be displayed again by unchecking.

As just described, the confirmation operation by the user can be effectively supported by switching and displaying the plurality of stained images included in the image set while reflecting the result of the registration processing between those. By enabling the switch of the display/non-display of the image and the change of the display order to be done by the user operation, the operation can be made more efficient.

A combination of one image stack S and the results of the registration processing by a single recipe can be used as the image set. It is also possible to use an integration of one image stack S and the results of the registration processings of a plurality of recipes for the image stack S. If the recipes of the registration processings are different, values of obtained registration amounts are possibly different even between two stained images included in the same image stack S.

For the purpose of registration between two images, the registration processing is desirably performed by using a recipe capable of precisely extracting differences of those images. Accordingly, if an operation of integrating the results of the registration processings by a plurality of recipes and extracting the best result, out of those, is performed, it is convenience. To this end, it is, for example, considered to define a combination of one image stack S and the results of the registration processing by one recipe as one image subset and define a collection of a plurality of image subsets obtained by applying different recipes to the same image stack S as one image set.

For example, when the registration processing between two images Image001 and Image002 is considered, the registration amount obtained by the recipe 1 and the registration amount obtained by the recipe 2 do not necessarily coincide. Thus, when the image to be displayed is switched, for example, from the image Image001 to the image Image002 in the image display processing of reflecting the result of the registration processing, the position of the image Image002 is possibly different when the result of the registration processing by the recipe 1 is reflected and when the result of the registration processing by the recipe 2 is reflected.

The recipe having a smaller position shift amount after the registration processing from the image Image001 can be said to give a better result between these images. By appropriately selecting a combination of preceding and succeeding images in the switch display, superiority or inferiority between such recipes can also be compared. By adopting the registration amounts of the recipe providing a better result among the plurality of recipes, the accuracy of the registration processing for the image stack S can be improved.

In the integration of the image subsets, if the image sets generated for each recipe are directly integrated as described above, the number of the stained images to be confirmed increases and time and effort for the confirmation operation largely increase. To solve this problem, it is also possible to constitute an image set by collecting only the stained images selected from each image subset by the user as described next. Here, it is assumed that a plurality of image subsets corresponding to the plurality of recipes are generated for the single image stack S.

Figure 10:
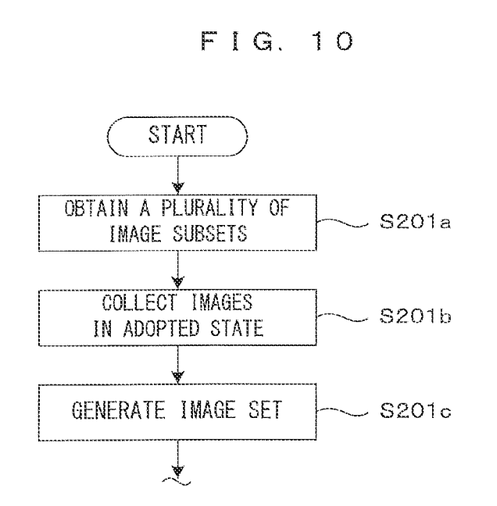
FIG. 10 is a flow chart partially showing an example of generating one image set from a plurality of image subsets.

FIG. 10 is a flow chart partially showing an example of generating one image set from a plurality of image subsets. This processing can be realized by replacing Step S201 in the processing of FIG. 3 by processings of Steps S201a to S201c shown in FIG. 10. In Step S201a, the plurality of image subsets associated with the results of the registration processings are obtained using different recipes for the same image stack S. Then, out of the stained images included in each image subset, only the images in the adopted state are collected (Step S201b) and the image subset composed of those images is generated (Step S201c).

Figure 11:
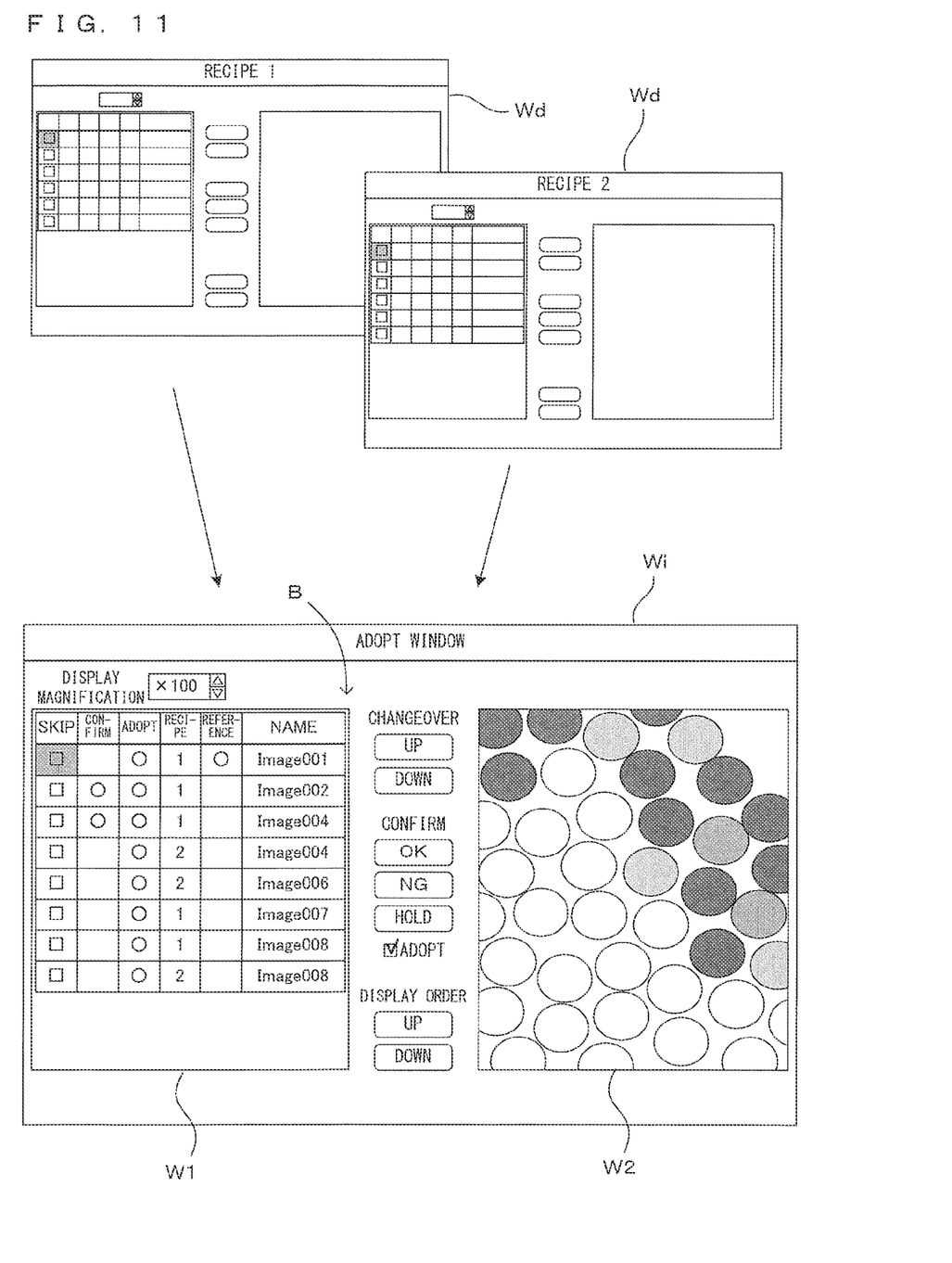
FIG. 11 is a view showing a display example of the integrated image set.

FIG. 11 is a view showing a display example of the integrated image set. As shown in FIG. 11, the image display processing of FIG. 3 is performed in parallel for each of the image subsets corresponding to the difference recipes (recipe 1, recipe 2) and the display for that is made on the same screen as an individual window Wd for each recipe.

In an "adopt window" Wi showing the integrated image set, the images in the adopted state are extracted from the respective subsets and listed up in the list window W1. It is more preferable that an operation result on the screen corresponding to each of the recipes 1, 2 is immediately reflected in the adopt window. That is, when a certain image is set in the adopted state, for example, on the screen corresponding to the recipe 1, this image is immediately incorporated into the list window W1 in the adopt window W1.

Numbers "1", "2" shown in the column "RECIPE" in the list window W1 in the adopt window Wi respectively indicate the images selected from the recipes 1, 2. As just described, even the same stained image is handled as different images in the image set if the registration processings applied are different.

As just described, the display of the individual windows Wd respectively corresponding to the different recipes and the display of the adopt window Wi integrating those individual windows Wd are made simultaneously. By doing so, the confirmation operation in each recipe and the confirmation operation over the plurality of recipes can proceed in parallel. For example, the accuracy of the registration results for the image stack S can be improved by collecting only the images determined to be succeeded in the registration processing in each recipe into the adopt window (corresponding to an "integration window" of the invention) Wi. This is because an operation of comparing the registration results in the plurality of recipes and selecting the best registration result, out of those, is possible.

Further, this display mode is usable also for the purpose of evaluating the recipe of the registration processing. That is, it can be said that the recipe including more images judged as a "success" as a result of the above operation using the registration processings in the plurality of recipes can provide the most effective registration processing for the image stack S.

Note that, in this embodiment, the displayed image is switched according to the changeover button operation by the user. Besides this, a display mode for automatically switching the images at certain time intervals is convenient. For example, there is a need to grasp the overall tendency of the results of the registration processing among many images or a rearranging operation of the display order proceeds to a certain extent and those are confirmed. In this case, the user can successively confirm the respective images without taking his/her eyes off from the image window W2 by automatically switching the display.

Accordingly, it is preferable to provide both the display mode for switching the images by the user operation as described above and the display mode for automatically switching the images at certain time intervals. It is more preferable to enable the selection of either one according to the user's desire.

As described above, in the image display method of this embodiment, each stained image is switched and displayed while the registration result is reflected for the image set including the plurality of stained images, for which the registration processing was performed. In this way, the confirmation operation of the registration results by the user can be effectively supported using the afterimage effect.

To effectively use the afterimage effect, a switch rule for determining a combination of the images to be switched and displayed is changeable. That is, a function of excluding some images from the images to be switched and displayed, a function of changing the display order and the like are executable according to the user operation. Further, the determination result of the user on the success or failure of the registration processing can be recorded while the images are switched and displayed. By these functions, the confirmation operation by the user can be more efficiently performed and a workload of the user is also reduced.

Various image processings in the above embodiment can be executed using a computer device having a general hardware configuration. That is, by implementing a computer program describing the above operation procedure in a general-purpose computer device, this computer device can be caused to function as an executor of the invention.

Note that the invention is not limited to the embodiment described above and various changes other than the aforementioned ones can be made without departing from the gist of the invention. For example, the display screen configuration of the above embodiment shows an example thereof. The arrangements, names and the like of the windows and buttons are arbitrary without being limited to those described above. Further, such a function as to simultaneously display a plurality of stained images in the image window may be, for example, further provided.

Further, besides the method for operating the display order buttons as described above to change the display order in the image window W2, a method for moving the display order by drag and drop in the list window W1 may be, for example, added.

As the specific embodiment has been illustrated and described above, the image display method according to the invention can be configured to receive a designation for distinguishing, out of a plurality of stained images, the stained images to be displayed on the screen and the stained images to be excluded as an operation input. When the user confirms by switching and displaying the plurality of stained images, these stained images possibly include the images, which become an obstacle in confirming the other images, such as the images having light-and-shade patterns largely different from those of the other images and the images having an improper result of the registration processing. By making it possible to exclude such images from the images to be displayed, the confirmation operation of the other images can be more efficiently performed.

Further, a designation on the order of the stained images to be displayed on the screen can be received as an operation input. A function of moving the display order of the stained images designated by the operation input may be provided. By receiving a change of the display order, the images desired to be compared with each other by the user can be switched and displayed in a desired order.

Further, for example, the first stained image in the display order set by the switch rule may be displayed next to the last stained image in the display order. According to such a configuration, the stained images distant in the display order can be switched and compared.

Further, for example, the mode for switching the displayed images according to the user operation and the mode for automatically switching the displayed images at predetermined time intervals may be executable as the mode for switching and displaying the stained images. Since the display is not switched until the user operation is given in the display switch by the user operation, one image can be observed for a desired time. On the other hand, in the mode for automatically switching the display, the user can confirm many images without taking his/her eyes off from the screen. Particularly, in the case of comparing the images using the afterimage effect, it is useful to be able to fix a gaze.

Further, for example, an operation input from the user on the determination result of the registration processing can be received for the stained image to be displayed on the screen. In this way, information on the user's determination for the result of the registration processing can be given to each stained image.

Further, for example, the image set may include a plurality of subsets obtained by applying the registration processings having different processing conditions to the same set of stained images. Even if the stained images are in the same set, the registration results may be different if the processing conditions of the registration processings are different. By using the image set including the plurality of subsets having different processing conditions, it is possible to extract and select a good result, out of those subsets, and adopt the selected result as the result of the registration processing.

In this case, the screen display of switching and displaying the stained images included in one subset and the screen display of switching and displaying the stained images included in the plurality of subsets can be performed. Further, for example, a plurality of individual windows respectively corresponding to the plurality of subsets and an integration window for displaying the stained images selected from the individual subsets by the user operation using the individual windows in an integrated manner may be provided as windows for displaying the stained images. By so doing, it is possible to perform a confirmation operation in one subset and a confirmation operation over the subsets.

Further, for example, the stained images selected by the operation input from the user, out of the stained images included in the plurality of subsets, may be included in the image set. Since the image set includes the plurality of subsets, the number of the images to be displayed may increase and time and effort for the confirmation operation may increase. Accordingly, if the stained images to be included in the image set are made selectable by the user, the user can collect only the images judged necessary to be confirmed over the subsets and configure the image set, and the efficiency of the confirmation operation can be improved.

Note that the invention can be carried out in the form of a computer-readable recording medium recording this program non-transitorily as a computer program for causing a computer device to perform each step of the image display method described above. Each of the above steps is realizable by a computer device having a general hardware configuration and, by implementing the above program in an existing computer, a new function can be given to this computer device.

This invention is applicable to integrate and analyze images obtained by staining and imaging the same tissue specimen a plurality of times in the field of medical/biological research and the like and is, for example, suitable for the analysis of a multiple immunostained tissue specimen in single cells.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

What is claimed is:

1. An image display method, comprising:
obtaining an image set including a plurality of stained images, the plurality of stained images being obtained by imaging a multiple immunostained tissue specimen and a registration processing being performed for mutual registration for the plurality of stained images;
displaying, on a screen, an image including at least one of the stained images and a graphical user interface for receiving an operation input from a user to edit a switch rule for determining a combination of the stained images to be switched and displayed;
receiving the operation input from the user and changing the switch rule according to the operation input; and
displaying the stained included in the image set alternately with a result of the registration processing reflected by switching the stained images in a same window in the screen in accordance with the switch rule after changing.

2. The image display method according to claim 1, wherein a designation for distinguishing the stained images to be displayed on the screen and the stained images to be excluded out of the plurality of stained images is received as the operation input.

3. The image display method according to claim 1, wherein a designation on an order of the stained images to be displayed on the screen is received as the operation input.

4. The image display method according to claim 1, wherein a first stained image in a display order set by the switch rule is displayed next to a last stained image in the display order.

5. The image display method according to claim 1, wherein as modes for switching and displaying the stained images, a mode for switching displayed images according to a user operation and a mode for automatically switching displayed images at predetermined time intervals is executable.

6. The image display method according to claim 1, wherein the operation input from the user on a determination result of the registration processing is received for the stained image to be displayed on the screen.

7. The image display method according to claim 1, wherein the image set includes a plurality of subsets obtained by applying the registration processings having different processing conditions to a same set of stained images.

8. The image display method according to claim 7, wherein a screen display of switching and displaying the stained images included in one subset and a screen display of switching and displaying the stained images included in the plurality of subsets is executable.

9. The image display method according to claim 7, wherein as windows for displaying the stained images, a plurality of individual windows respectively corresponding to the plurality of subsets and an integration window for displaying the stained images selected from individual subsets by a user operation using the individual windows in an integrated manner are provided.

10. The image display method according to claim 7, wherein the stained images selected by the operation input from the user, out of the stained images included in the plurality of subsets, are included in the image set.

11. A computer-readable recording medium, storing non-transitorily a computer program for causing a computer to perform the image display method according to claim 1.

\* \* \* \* \*